US009799009B2

(12) United States Patent
Hobbs et al.

(10) Patent No.: US 9,799,009 B2
(45) Date of Patent: Oct. 24, 2017

(54) METHOD AND SYSTEM FOR DETERMINING EXPOSURES PRESENTED BY AN ORCHESTRATED PROCESS

(75) Inventors: Christopher Hobbs, Ottawa (CA); John Bell, Ottawa (CA); Raymond B. Wallace, Ashton (CA); Laurence A. Beaulieu, Kanata (CA)

(73) Assignee: Avaya Inc., Basking Ridge, NJ (US)

( * ) Notice: Subject to any disclaimer, the term of this patent is extended or adjusted under 35 U.S.C. 154(b) by 1776 days.

(21) Appl. No.: 11/947,990

(22) Filed: Nov. 30, 2007

(65) Prior Publication Data
US 2009/0144077 A1 Jun. 4, 2009

(51) Int. Cl.
*G06Q 10/06* (2012.01)
*G06Q 10/10* (2012.01)
*G06Q 50/22* (2012.01)

(52) U.S. Cl.
CPC ......... *G06Q 10/1095* (2013.01); *G06Q 10/10* (2013.01); *G06Q 50/22* (2013.01)

(58) Field of Classification Search
CPC .............. G06Q 10/06; G06Q 10/06311; G06F 17/5009
USPC ........................................ 700/2–3
See application file for complete search history.

(56) References Cited

U.S. PATENT DOCUMENTS

| 5,764,953 | A | * | 6/1998 | Collins ................ G06Q 10/06 703/17 |
| 5,960,337 | A | * | 9/1999 | Brewster ................ A61K 31/02 342/386 |
| 7,729,928 | B2 | * | 6/2010 | Backhaus ............. G06F 19/327 705/2 |
| 2002/0107769 | A1 | * | 8/2002 | Dashefsky ............. G06Q 10/04 705/35 |
| 2002/0116220 | A1 | * | 8/2002 | Glazier ................ G06F 19/327 705/2 |
| 2003/0074222 | A1 | * | 4/2003 | Rosow .................. G06Q 10/02 705/2 |
| 2004/0008125 | A1 | * | 1/2004 | Aratow ................ G06Q 50/265 340/870.07 |
| 2006/0031110 | A1 | * | 2/2006 | Benbassat ............. G06Q 10/06 705/7.14 |
| 2007/0129927 | A1 | * | 6/2007 | Chussil .................. G06N 3/004 703/16 |

(Continued)

OTHER PUBLICATIONS

Anagnostopoulosa et al., Timing Issues and Experiment Scheduling in Faster-Than-Real-Time Simulation, Nov. 2003, Simulation, 79(11): 613-625.*

*Primary Examiner* — Joy Chng

(57) ABSTRACT

The present invention provides a system and method to dynamically identify, assemble, or otherwise simulate the availability of resources for an orchestrated service or application, thereby allowing for strategic changes in scheduling, purchasing, hiring, and the like to ensure that the resources needed to deliver the desired outcome during a particular time period are present. In particular, the system includes an orchestration module storing a plurality of resource parameters, correlating a predetermined criterion for one or more resources with an event, and simulating the event, where the simulation includes comparing the stored plurality of parameters with the predetermined criterion. The system further determines whether the stored plurality of parameters satisfy the predetermined criterion, and may store the determination for subsequent evaluation.

18 Claims, 4 Drawing Sheets

(56) References Cited

U.S. PATENT DOCUMENTS

2008/0114408 A1\* 5/2008 Shuros et al. .................. 607/11

\* cited by examiner

METHOD AND SYSTEM FOR DETERMINING EXPOSURES PRESENTED BY AN ORCHESTRATED PROCESS

CROSS-REFERENCE TO RELATED APPLICATION

N/A

STATEMENT REGARDING FEDERALLY SPONSORED RESEARCH OR DEVELOPMENT

N/A

FIELD OF THE INVENTION

The present invention relates to orchestrated service solutions, and in particular, a system and method for simulating an orchestration of a plurality of services to determine resultant exposures.

BACKGROUND OF THE INVENTION

Within a system based on a service-oriented architecture, new services are often created by combining existing services together in a new way. Depending on the exact method of service combination, this technique might be known as orchestration, choreography or "mashing-up". Orchestration usually involves some central control mechanism that invokes or otherwise involves numerous underlying services to provide an overall, composite result or desired outcome. Such orchestration allows new solutions or services to be assembled or compiled relatively quickly by redistributing and/or combining a palette of existing, underlying services.

For example, consider a service or application for assembling resources in response to a particular event, e.g., assembling personnel to respond to an emergency, compiling equipment needed for a task, etc. An initial action triggers or otherwise invokes the orchestrated resource assembly service. This, in turn, actuates underlying location, database, messaging, mapping, logging and/or other additional services to identify and select available resources, provide instructions, log the actions taken for audit purposes, etc.

The particular application or service may be invoked infrequently (perhaps once a day, perhaps once a year) and, as with any infrequently-utilized system, the issue arises as to whether the system or service is able to successfully deliver the desired result, e.g., are the required resources available, are the items needed operational, etc. In other words, there is an ever-present risk that an idle or typically offline resource has failed silently during the period of non-use and/or is otherwise simply unavailable. The condition of an undetected failure or lack of availability can have disastrous consequences depending on the particular nature and environment in which the orchestration system is being utilized. In a business setting, for example, unavailable resources may lead to a loss of profit or productivity, while in a healthcare setting, if an emergency occurs and the needed resources are unavailable, the result could be a loss of life.

To reduce the likelihood of failure or unavailability, systems or events may be routinely enacted or tested through a "fire drill," or the like, where the actual service or resources are enacted to perform their duties under a simulated assumption that a triggering event has occurred. However, even though the actual event or condition to which the systems, applications, or resources must respond has not actually occurred, the resources are nonetheless then occupied with performing their assumed duties during the drill, which prevents them from completing actual tasks or responding to actual events. In other words, while a practice drill may ensure operational capacity or availability of certain resources, during such a practice drill these resources are unable to complete other tasks, which increases inefficiency as well as loss of productivity.

In view of the above, it is desirable to have a system and method to gauge or otherwise simulate an orchestrated service or procedure to determine the availability of resources, thereby allowing for strategic changes in scheduling, purchasing, hiring, and the like to ensure that the resources needed to deliver the desired outcome during a particular time period are indeed present, without occupying the actual resources to do so.

SUMMARY OF THE INVENTION

The present invention advantageously provides a method for assessing resource availability, including monitoring at least one parameter corresponding to one or more resources; correlating a predetermined criterion for one or more resources with an event; simulating the event, wherein the simulation includes comparing the monitored parameter with the predetermined criteria, and determining whether the monitored parameter satisfies the predetermined criteria. The method may further include repeatedly simulating the event at predetermined or dynamically-chosen time intervals, and monitoring at least one parameter of at least one resource in real-time. In addition, the determination of whether the monitored parameter satisfies the predetermined criteria may be stored, and a threshold for the determination that the monitored parameter does not satisfy the predetermined criteria may defined. Subsequently, the method may include generating an alert in response to the threshold being one of equaled and exceeded.

The present invention also provides a method for assessing resource availability, including communicating a plurality of parameters corresponding to a plurality of resources; storing the plurality of parameters corresponding to the plurality of resources; correlating a predetermined criterion for one or more resources with an event; simulating the event, the simulation including comparing the stored plurality of parameters with the predetermined criterion; and determining whether the stored plurality of parameters satisfies the predetermined criterion. The plurality of resources may include medical resources located at a medical facility, and the event may be a medical or healthcare-related event. The method may further include repeatedly simulating the event at predetermined time intervals, as well as monitoring the plurality of parameters in real-time. The method may also analyze or otherwise use monitored information to calculate intervals at which it would be advantageous to repeat the simulation and use such dynamically calculated intervals rather than a fixed, predetermined time interval. The determination of whether the stored parameters satisfy the predetermined criteria may be stored, and an identification of one or more of the plurality of resources having a parameter that satisfies at least a portion of the predetermined criteria can be made. In addition, a threshold for the determination that the plurality of parameters does not satisfy the predetermined criteria may be defined, and an alert may be generated in response to the threshold being one of equaled and exceeded.

The present invention further provides a system for orchestrating a plurality of resources, including one or more auxiliary modules transmitting a plurality of parameters correlating to the plurality of resources across a communication network; and an orchestration module storing the transmitted plurality of parameters; correlating a predetermined criteria for one or more resources with an event; simulating the event, the simulation including comparing the stored plurality of parameters with the predetermined criteria; and determining whether the stored plurality of parameters satisfy the predetermined criteria. The orchestration module may repeatedly simulate the event at predetermined or dynamically calculated time intervals, and the transmitted plurality of parameters may correlate to a real-time disposition of the plurality of resources. Moreover, the orchestration module may store the determination of whether the stored parameters satisfy the predetermined criteria. The orchestration module may include a threshold for the determination that the stored parameters do not satisfy the predetermined criteria, and may also generate an alert in response to the threshold being one of equaled and exceeded. The plurality of resources can include medical resources located at a medical facility.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
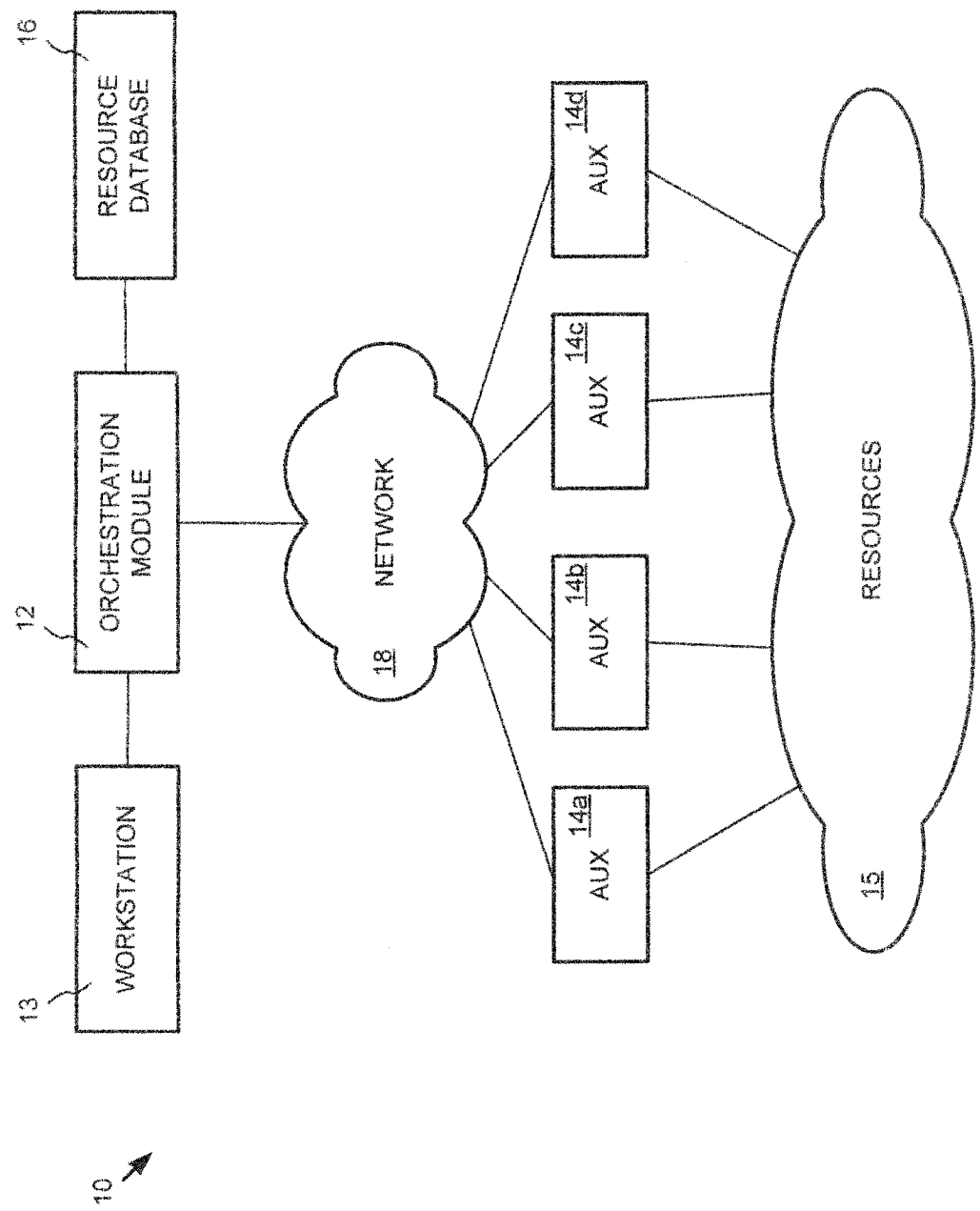
FIG. 1 is an illustration of an embodiment of a system in accordance with the present invention.

The present invention provides a system and method to dynamically identify, assemble, or otherwise simulate the availability of resources for an orchestrated service or application, thereby allowing for strategic changes in scheduling, purchasing, hiring, and the like to ensure that the resources needed to deliver the desired outcome during a particular time period are present. Referring now to the drawing figures in which like reference designators refer to like elements, there is shown in FIG. 1, a service orchestration system constructed in accordance with the principles of the present invention and designated generally as "10". In particular, the system 10 of the present invention includes an orchestration module 12 that interacts with one or more auxiliary modules 14a, 14b, 14c, 14d . . . (collectively referred to as auxiliary modules 14) to dynamically monitor, store and/or manipulate data, information, and/or characteristics regarding certain resources 15, and to direct the allocation of those resources under certain circumstances. As used herein, the term 'resource' is intended to encompass an element of supply, support, or aid that can be drawn upon when needed, and includes but is not limited to personnel, equipment, tools and the like integral to producing a desired service or output corresponding to a particular event.

Either and/or both the orchestration module 12 and the auxiliary modules 14 can include hardware components, software components, or a combination of hardware and software components. For example, an implementation of the orchestration module 12 and the auxiliary modules 14 can be implemented in a centralized fashion in one computing system, or in a distributed fashion where the orchestration module 12 and the auxiliary modules 14 are spread across several interconnected computing systems. The orchestration module 12 may include an application or operating environment accessible through one or more hardware workstations 13, for example. Of course, any kind of computing system, or other apparatus adapted for carrying out the methods described herein, is suited to provide the features and perform the functions described herein.

The orchestration module 12 may store information related to one or more resources 15 available in a particular application or system. In particular, the orchestration module 12 may include the recording and/or storing of resource-particular information or have access to a service providing resource-particular information, including but not limited to an overall label or description of a resource, a capacity of the resource to perform a particular function or task ("experienced with cardiac conditions"), a location of the resource on a micro or macro level (e.g., "on the $9^{th}$ floor," or "in City X"), a current status of the resource (available, offsite—unavailable, present but incapacitated, inoperable, busy, etc.), and any other pertinent characteristic or property of a resource at a given time. The information and characteristics may be stored in a resource database 16 integrated with and/or accessible by the orchestration module 12 and/or the auxiliary modules 14. The resource database may reside within an operating environment or computing system similar to the orchestration module 12, and/or may be stored on a computer readable storage media otherwise accessible by the orchestration module 12 and the auxiliary modules 14 via a communication network. Moreover, the resource database 16 may be updated in real-time to reflect changes or developments regarding the status or disposition of particular resources.

The particular information or status concerning a resource may be relayed or otherwise provided to the orchestration module 12 through a wired or wireless communication network 18 from the auxiliary modules 14. The communication network 18 may include the capacity for SMS messaging, telephone, wireless communication, paging, instant messaging or the like and may operate with various communication protocols, such as TCP/IP or the like. The auxiliary modules 14 may include subsystems and/or programs involved in monitoring, providing and/or tracking information concerning the resources, and communicating such information to the orchestration module 12. For example, an auxiliary module having a locator function may interact with a particular resource to monitor its location, through GPS for instance, and the location information may be subsequently relayed to the orchestration module 12. In a similar example, an auxiliary module 14 having a scheduling capacity may monitor and/or otherwise include information related to the scheduling of when a particular resource is online, available to provide coverage, etc. Additional modules may interact with and/or provide contextual data concerning the particular resources as needed in a specific application of the present invention.

Figure 2:
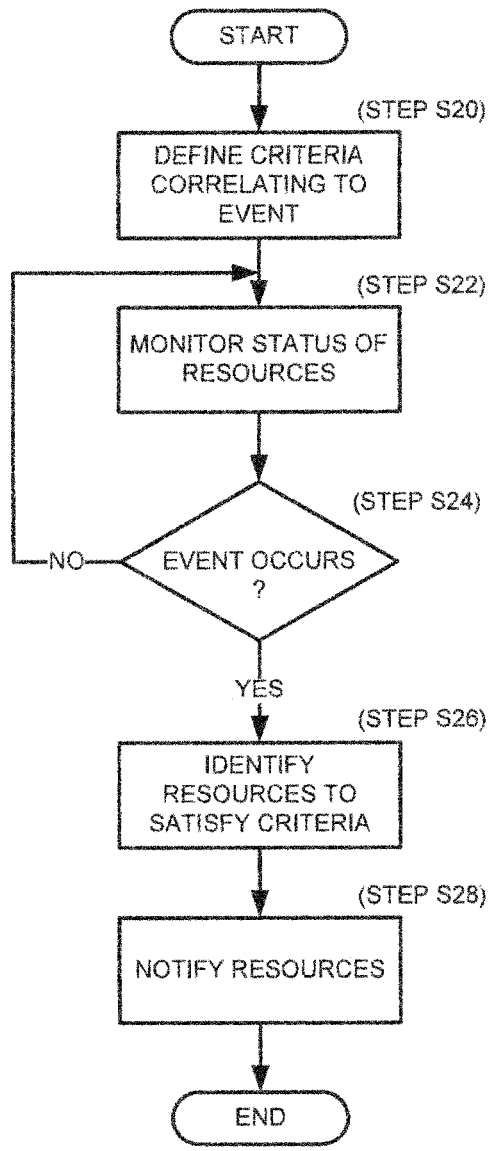
FIG. 2 is a flow chart of an embodiment of a method of allocating resources at the occurrence of an event in accordance with the present invention.

The orchestration module 12 may interact with the one or more auxiliary modules 14 to coordinate the allocation and/or integration of resources in response to an actual or simulated event. FIG. 2 is a flow chart of an exemplary method of an orchestrated service triggered by an event. In particular, the orchestration module 12 may be configured with a predetermined set of parameters or criteria related to applicable resources 15 required or desired for a particular condition or event (Step S20), or may learn these dynamically by observation of manually-initiated responses to the same condition or event. For example, in the occurrence of event 'X,' resources A, B and C should be transported or otherwise positioned at location 'Y.' The status and/or condition of the resources 15 defined in the criteria are monitored or logged (Step S22). Upon the occurrence of an actual event (Step S24), the orchestration module 12 may identify the needed or available resources (Step S26), and communicate instructions or an indication of the event to the particular resources corresponding to the predetermined criteria (Steps S28). Should the circumstance be that there are insufficient resources available to satisfy the predetermined criteria correlating to a particular event, instructions or an alert may be conveyed to the resources that are available, and an indication of the inability to wholly satisfy the predetermined criteria may also be conveyed to one or more appropriate recipients. The communication may occur through the communication network 18, and may also occur through the auxiliary modules 14 described above. The resources 15, in turn, may then respond accordingly to the indication that the prescribed triggering event has occurred.

Figure 3:
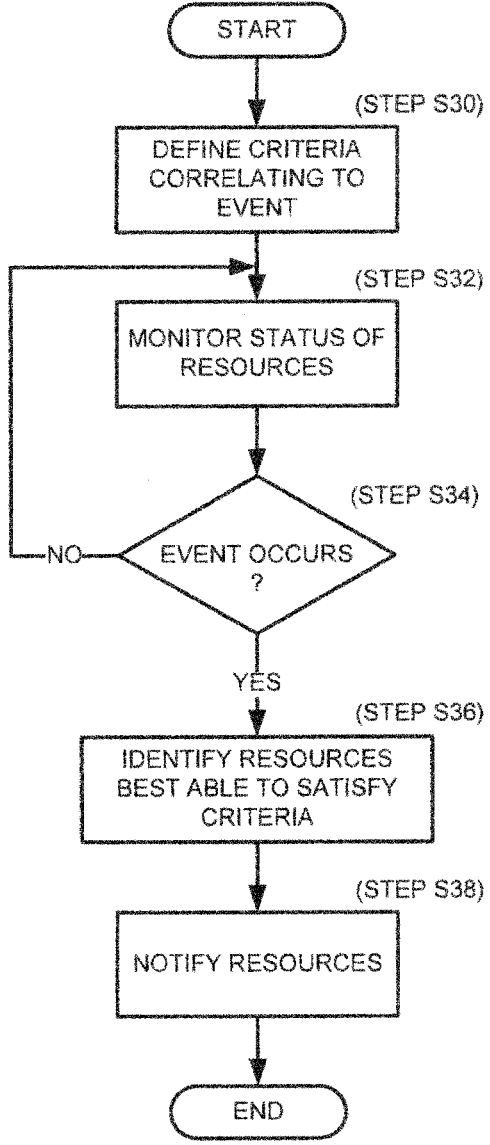
FIG. 3 is a flow chart of an embodiment of a method of dynamically allocating resources at the occurrence of an event in accordance with the present invention.

The system of the present invention may further provide for the dynamic selection and/or allocation of available resources in the occurrence of an event based on the real-time disposition or status of those available resources and other events occurring at the same time that may be consuming the same resources. Now referring to the flow chart of FIG. 3, the orchestration module 12 may be configured with a predetermined set of parameters or criteria related to applicable resources required or desired for a particular condition or event (Step S30). Moreover, the status and/or particular disposition of a resource is monitored or relayed to the orchestration module 12 via the one or more auxiliary modules 14 and stored in the resource database 16 (Step S32). When the prescribed event occurs (Step S34), the predetermined resource criteria correlating to that event may be referenced and compared to the current resource status stored in the resource database 16. The orchestration module 12 may then select or otherwise identify one or more resources 15 among the total available resources satisfying the predetermined criteria that are best suited to respond to the event (Step S36), and instructions or an alert of the occurrence of the event may be conveyed to the selected resources so they may respond appropriately (Step S38). For example, the selection by the orchestration module 12 may be based on various characteristics or properties attributed to the resources 15, such as proximity to the response location, capacity of the resource to handle volume of response, past performance, etc. Should the circumstance be such that there are insufficient resources available to satisfy the predetermined criteria correlating to a particular event, instructions or an alert may be conveyed from the orchestration module 12 to the resources that are available via the auxiliary modules 14 and/or the communication network 18, and an indication of the inability to wholly satisfy the predetermined criteria may also be conveyed to one or more appropriate, predetermined recipients (the identity of which may also be stored in the resource database 16 or be included in the initial criteria set forth in the orchestration module 12 for a particular event). By selecting or identifying those resources best suited to respond or perform their function, efficiency of the service or response to the event may be enhanced.

Figure 4:
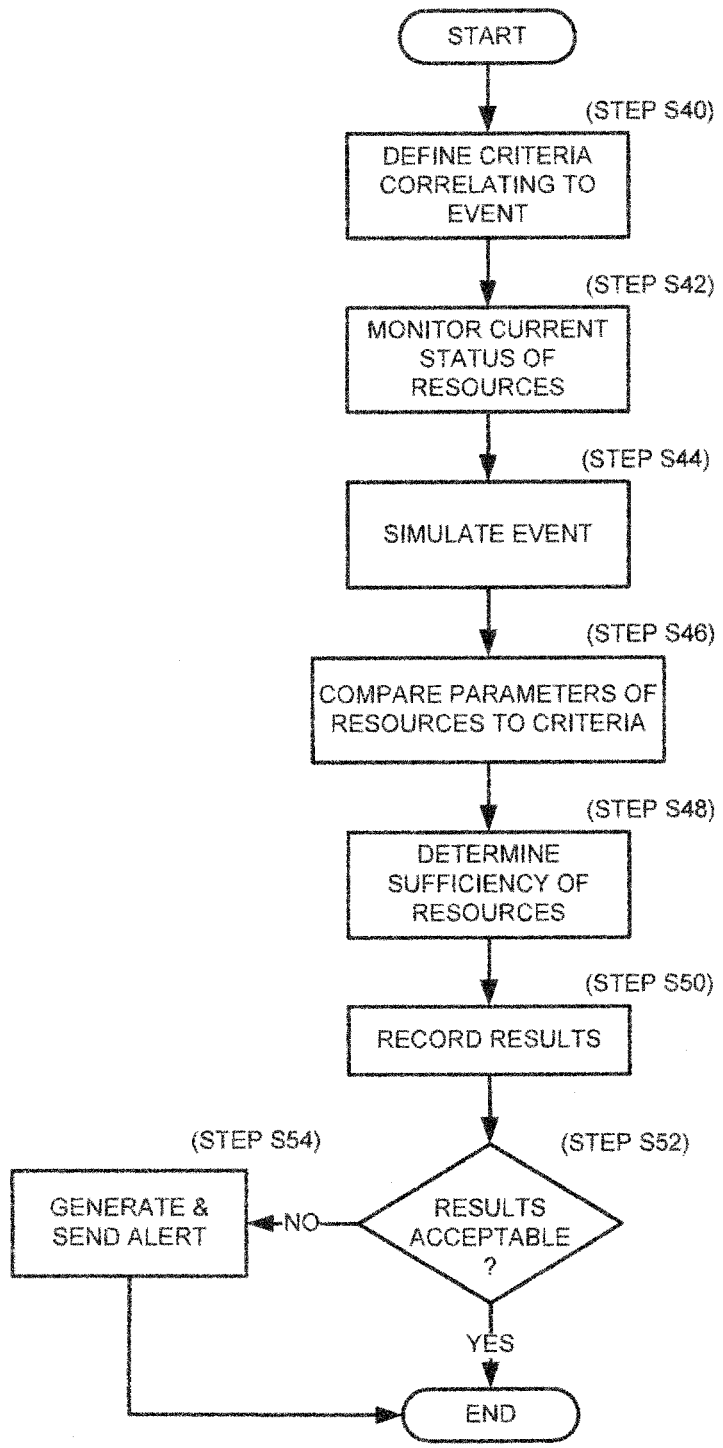
FIG. 4 is a flow chart of an embodiment of a method of identifying resource availability at the occurrence of a simulated event in accordance with the present invention.

The present invention may further include the simulation of an event to determine whether resources slated to respond or provide a specialized function in the occurrence of such an event would be available to respond. Now referring to FIG. 4, in particular, the orchestration module 12 may be configured with a predetermined set of parameters or criteria related to applicable resources required or desired for a particular condition or event (Step S40), such as first responders, their equipment, and a location for service, for example. Moreover, the real time status and/or actual particular disposition of a resource is monitored or relayed to the orchestration module 12 via the one or more auxiliary modules and stored in the resource database 15 (Step S42). Subsequently, the orchestration module 12 may simulate the occurrence of an event at predetermined, dynamically calculated or random time intervals to determine a capacity to respond at any given moment (Step S44). The 'simulation' may result in a comparison of the predetermined set of parameters or criteria related to applicable resources required or desired for a particular condition or event to the information regarding the resources stored in the resource database (Step S46), which may be dynamically updated in real-time via the one or more auxiliary modules. Upon comparing the predetermined criteria to the existing status or condition of the pertinent resources, a determination may be made as to whether sufficient resources are available to successfully respond to the event (Step S48), and the success or failure of the simulation may be recorded or compiled for subsequent evaluation (Step S50). The simulation of the event does not necessarily include the actual communication of instructions or allocation of particular resources as in an actual event, and accordingly, the simulation and/or comparison of actual resource disposition with the desired criteria may be executed as frequently as needed to determine patterns of unavailability or assess a decreased capacity to respond. Upon compiling and/or storing the results of the comparison between the actual resource disposition or availability and the desired criteria correlated to an event, strategic changes in scheduling, purchasing, hiring, and the like can be informatively pursued to ensure that the resources needed to deliver the desired outcome or service during a particular time period are present. In addition, the success or failure of the simulation over a particular time period may be used as a basis for modifying or dynamically changing the intervals at which the simulation is performed. Moreover, a threshold may be defined as to the acceptable level or frequency of resource unavailability or insufficiency (Step S52), and an alert may be generated and conveyed to appropriate recipients when that threshold is equaled or exceeded (Step S54).

In an exemplary application, the system and method of the present invention may be employed in a healthcare setting, such as a hospital. A hospital includes various types and kinds of resources, including medical personnel such as doctors and nurses, security personnel, as well as equipment and tools, such as ventilators, defibrillators, electrocardiograph machines, etc. The orchestration module 12 can maintain information regarding the resources 15 within the hospital, as provided by one or more of the auxiliary modules 14. For example, the tools and equipment may have designated areas in which they are stored when not in use, and may also include a locating mechanism to provide an up-to-the-minute physical location of the device or equipment. In addition, an employee schedule may detail when certain personnel are on duty or at work. This information may be relayed to the orchestration module 12 and stored in the resource database 16. Of course, additional details and information of the hospital resources may be conveyed to the orchestration module 12 as needed or deemed appropriate.

As stated above, the orchestration module 12 may be configured with a predetermined set of parameters or criteria related to applicable resources required or desired for a particular condition or event. For example, in the event of a cardiac arrest of a patient in the hospital, the orchestration module 12 may be configured or programmed to correlate the predetermined criteria of having an attending nurse, a defibrillator, and a cardiologist report to the room of the patient to administer treatment. When an actual cardiac arrest occurs, it may be triggered by a patient monitoring device, an emergency call button, or other triggering mechanism, which alerts or otherwise actuates the orchestration module to reference the predetermined criteria for the event, as well as the resource database housing the resource status.

In general, if the resources needed for the cardiac arrest are available, i.e., the nurse, defibrillator, and cardiologist are able to respond, then instructions or an alert may be conveyed to institute action. Should the circumstances exist that numerous resources are available to respond to a particular cardiac arrest event, then the orchestration module 12 may compare one or more characteristics of the available resources to identify and select which of the available resources would be best suited to respond. For instance, there may be several nurses available, but one nurse in particular is located on the floor, or portion of the floor, that the patient in need of care is located and therefore could respond the fastest. Moreover, supposing there are multiple cardiologists available, the orchestration module may compare schedules (i.e., cardiologist #1 may be available, but be scheduled for surgery in 10 minutes), previous interactions with a particular patient (i.e., cardiologist #2 has treated the patient before), or the like to make a selection and thereafter notify the selected cardiologist of the cardiac event. Of course, should the circumstance be that there are not sufficient resources available to satisfy the predetermined criteria for the cardiac arrest, instructions or an alert may be conveyed to the resources that are available, and an indication of the inability to wholly respond to the patient may also be conveyed to an appropriate recipient, such as any other available personnel or resource (regardless of skill set, for instance) in the vicinity.

In the case of a simulated cardiac arrest, the orchestration module 12 may compare the correlated predetermined criteria to the status or condition of resources listed in the resource database 16 to make a determination of whether the predetermined criteria could be satisfied at that particular moment. The result of the determination may then be stored for later analysis. For the simulated event, no actual resources are notified or directed to act, so the simulation could be executed repeatedly over regularly or irregularly scheduled time intervals. Subsequently, patterns of any incapacity or insufficient resource availability could be noted, such as, "On Wednesdays between 10:00 am and 10:35 am, there are normally insufficient resources to respond to cardiac arrest should one occur," or, "The response time to provide a cardiac arrest response team to the 8$^{th}$ floor on Monday between 8:00 am and 8:15 am has a mean of 4 minutes and a distribution of X."

The information resulting from the simulation can provide temporal data on when resources are commonly not available, and may further be used to inform an appropriate recipient that a certain threshold of unavailability has been reached. By routinely and periodically assessing whether the predetermined criteria for a cardiac arrest could be met by the resources available, gaps in coverage and/or an assessment of overall risk involved in the inability to respond to the event can be identified and appropriate strategic changes can be made to reduce the incapacity or insufficiency to acceptable levels. Of note, while the above example has been provided in a healthcare setting, the system and method of the present invention are equally applicable in other service contexts involving the identification or allocation of resources.

The present invention can be realized in hardware, software, or a combination of hardware and software. An implementation of the method and system of the present invention can be realized in a centralized fashion in one computing system, or in a distributed fashion where different elements are spread across several interconnected computing systems. Any kind of computing system, or other apparatus adapted for carrying out the methods described herein, is suited to perform the functions described herein.

A typical combination of hardware and software could be a specialized or general purpose computer system having one or more processing elements and a computer program stored on a storage medium that, when loaded and executed, controls the computer system such that it carries out the methods described herein. The present invention can also be embedded in a computer program product that comprises all the features enabling the implementation of the methods described herein, and which, when loaded in a computing system is able to carry out these methods. Storage medium refers to any volatile or non-volatile computer readable storage device.

Computer program or application in the present context means any expression, in any language, code or notation, of a set of instructions intended to cause a system having an information processing capability to perform a particular function either directly or after either or both of the following a) conversion to another language, code or notation; b) reproduction in a different material form. In addition, unless mention was made above to the contrary, it should be noted that all of the accompanying drawings are not to scale. Significantly, this invention can be embodied in other specific forms without departing from the spirit or essential attributes thereof, and accordingly, reference should be had to the following claims, rather than to the foregoing specification, as indicating the scope of the invention.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method for dynamically assessing an availability of a plurality of resources designated to provide an orchestrated service, said method implemented by a computing system in communication with a resource database, said method comprising:

storing, in the resource database, resource information related to each of the plurality of resources, the resource information including at least one of: a description of the each resource, a capacity of the each resource to perform a function, a location of the each resource, and a current availability of the each resource for providing the orchestrated service;

updating, by the computing system, the stored resource information to reflect real-time changes in resource information for the each resource;

monitoring, by the computing system, at least one parameter corresponding to at least one resource of the plurality of resources, the at least one parameter specifying an availability of the corresponding at least one resource having the capacity to perform the function in the orchestrated service, the corresponding at least one resource being at least one of personnel and equipment;

correlating, by the computing system, an event to a predetermined resource criterion for one or more applicable resources of the plurality of resources, the one or more applicable resources being at least one of required and desired for the event, the predetermined resource criterion identifying the one or more applicable resources being best suited to use in response to an occurrence the event;

simulating, by the computing system, the event, wherein the simulation includes:
  specifying the event;
  designating at least one resource to respond to the event, the at least one designated resource including the one or more applicable resources; and
  comparing the monitored parameter with the predetermined resource criterion for each designated resource;

determining, by the computing system and after the simulation, whether the monitored parameter satisfies the predetermined resource criterion for each designated resource; and determining, by the computing system and after the simulation, a time interval for repeating the simulation based at least in part on the determination of whether the monitored parameter satisfies the predetermined resource criterion for each designated resource in the simulation, wherein:
  the determined time interval when the monitored parameter does not satisfy the predetermined resource criterion for the each designated resource is reduced relative to the time interval determined when the monitored parameter does satisfy the predetermined resource criterion for the each designated resource.

2. The method according to claim 1, further comprising repeatedly simulating, by the computing system, the event at the determined time intervals.

3. The method according to claim 1, further comprising monitoring, by the computing system, at least one parameter of at least one resource in real-time.

4. The method according to claim 1, further comprising storing, in the resource database, the determination of whether the monitored parameter satisfies the predetermined resource criterion.

5. The method according to claim 1, further comprising:
  defining, by the computing system, a threshold for the determination that the monitored parameter does not satisfy the predetermined resource criterion; and
  generating, by the computing system, an alert in response to the threshold being one of equaled and exceeded.

6. The method of claim 1, wherein the one or more of the plurality of resources includes a responder, and wherein determining whether the monitored parameter satisfies the predetermined resource criterion includes determining, by the computing system, whether the responder has experience with a patient that is a subject of the simulated event.

7. A method for dynamically assessing an availability of a plurality of resources designated to provide an orchestrated service, said method implemented by a communication network including a computing system in communication with a computer memory, said method comprising:
  communicating, via the communication network, a plurality of parameters corresponding to at least one resource of the plurality of resources, the plurality of parameters specifying an availability of the corresponding at least one resource having the capacity to perform a function in the orchestrated service, the corresponding at least one resource being at least one of personnel and equipment;
  storing, in the computer memory, the plurality of parameters corresponding to the at least one resource;
  simulating, by the computing system, the event, the simulation including:
    specifying the event;
    designating at least one resource to respond to the event, the at least one designated resource including the corresponding at least one resource having the capacity to perform a function in the orchestrated service; and
    comparing the stored plurality of parameters with a predetermined resource criterion for each designated resource;
  determining, by the computing system and after the simulation, whether the stored plurality of parameters satisfy the predetermined resource criterion for the designated resource; and
  determining, by the computing system and after the simulation, a time interval for repeating the simulation based at least in part on the determination of whether the stored plurality of parameters satisfy the predetermined resource criterion for each designated resource in the simulation, wherein:
    the determined time interval when the stored plurality of parameters do not satisfy the predetermined resource criterion for the each designated resource is reduced relative to the time interval determined when the stored plurality of parameters do satisfy the predetermined resource criterion for the each designated resource.

8. The method according to claim 7, further comprising monitoring, by the computing system, the plurality of parameters in real-time.

9. The method according to claim 7, further comprising storing, in the computer memory, the determination of whether the stored plurality of parameters satisfy the predetermined criterion.

10. The method according to claim 7, further comprising identifying, by the computing system, one or more of the plurality of resources having a parameter that satisfies at least a portion of the predetermined resource criterion.

11. The method according to claim 7, further comprising:
  defining, by the computing system, a threshold for the determination that the stored plurality of parameters do not satisfy the predetermined resource criterion; and
  generating, by the computing system an alert in response to the threshold being one of equaled and exceeded.

12. The method of claim 7, wherein one or more of the plurality of resources includes a responder, and wherein determining whether the stored plurality of parameters satisfy the predetermined resource criteria includes determining, by the computing system, whether the responder has experience with a patient that is a subject of the simulated event.

13. The method of claim 12, wherein determining whether the stored plurality of parameters satisfy the predetermined resource criteria includes determining, by the computing system whether the responder has responded to an event similar to the simulated event in the past.

14. A method of characterizing a response of a plurality of resources to a simulated emergency event, said method implemented by a communication network including a computing system in communication with at least one auxiliary module, the computing system further in communication with a resource database; said method comprising:
   storing, in the resource database, resource information related to each resource of the plurality of resources, the resource information including at least one of: a location of the each resource, an availability of the each resource for providing the orchestrated service, and a capacity of the each resource to perform a function, the each resource being at least one of personnel and equipment;
   receiving, via the communication network by the computing device from the at least one auxiliary module, a plurality of parameters specifying a current status of at least one resource of the plurality of resources, the current status including the resource information;
   updating, by the computing device, the stored resource information to reflect real-time changes in the current status of the at least one resource received by the computing device from the at least one auxiliary module;
   correlating, by the computing system, a non-simulated actual emergency event to a predetermined resource criterion for one or more applicable resources of the plurality of resources, the one or more applicable resources being at least one of required and desired for the actual emergency event, the predetermined resource criterion identifying the one or more applicable resources being best suited to use in response to an occurrence the actual emergency event;
   simulating, by the computing system, the actual emergency event, wherein the simulation includes:
      specifying the simulated emergency event;
      designating at least one resource to respond to the simulated emergency event, the at least one designated resource including the one or more applicable resources; and
      comparing the stored current status with the predetermined resource criterion for each designated resource;
   determining, by the computing system and after the simulation, whether the stored current status satisfies the predetermined resource criterion for each designated resource;
   determining, by the computing system, a time interval for repeating the simulation of the actual emergency event based at least in part on the determination of whether the stored current status satisfies the predetermined resource criterion for each designated resource in the simulation, wherein:
      the determined time interval when the stored current status does not satisfy the predetermined resource criterion for the each designated resource is reduced relative to the time interval determined when the stored current status does satisfy the predetermined resource criterion for the each designated resource; and
   determining, by the computing system and based at least in part on the determination of whether the stored current status satisfies the predetermined resource criterion for each designated resource in the simulation, a characteristic of a response to the occurrence of the actual emergency event based on the comparison, the characteristic indicating at least one of:
      whether the each designated resource successfully responded to the simulated emergency event; and
      whether at least one of a desired service or output corresponding to the simulated emergency event was produced by the response of the each designated resource.

15. The method of claim 14, wherein one or more of the plurality of resources includes a responder, wherein the stored current status includes a schedule of the responder stored in the resource database, and wherein comparing the stored current status with the predetermined resource criterion includes comparing, by the computing system, the stored schedule with the predetermined resource criterion.

16. The method of claim 15, wherein the responder is a surgeon and the schedule is a surgery schedule of the surgeon.

17. The method of claim 14, wherein:
   one or more of the plurality of resources includes a responder;
   the stored current status includes experience of the responder with at least one of:
      a patient that is a subject of the simulated emergency event; and
      a condition that is a subject of the simulated emergency event; and
   comparing the stored current status with the predetermined resource criterion includes comparing, by the computing device, the stored experience with the predetermined resource criterion.

18. The method of claim 14, further comprising:
   specifying, by the computing system, an objective of response to the simulated emergency event; and
   reporting, via the communication network, whether the objective can be met under simulated conditions.

* * * * *